United States Patent [19]

Kucher

[11] Patent Number: 4,546,782
[45] Date of Patent: Oct. 15, 1985

[54] COMBINATION TOOTHPICK, GUM MASSAGER, AND DENTAL FLOSS HOLDER

[76] Inventor: Carl J. Kucher, 111-33 123rd St., South Ozone Park, N.Y. 11420

[21] Appl. No.: 629,272

[22] Filed: Jul. 9, 1984

[51] Int. Cl.⁴ ............................................. A61C 15/00
[52] U.S. Cl. ......................................... 132/91; 132/89
[58] Field of Search .................................. 132/89–93, 132/84 D; 40/421

[56] References Cited

U.S. PATENT DOCUMENTS

| | | | |
|---|---|---|---|
| 2,925,087 | 2/1960 | Kucher | 132/93 |
| 4,094,328 | 6/1978 | Ray | 132/91 |
| 4,286,611 | 9/1981 | Talbot | 132/91 |
| 4,308,880 | 1/1982 | Graves | 132/91 |

Primary Examiner—Gregory E. McNeill
Attorney, Agent, or Firm—Richard L. Miller

[57] ABSTRACT

A combination toothpick, gum massager and dental floss holder which contains a toothpick, two teeth cleaning surfaces, a gum massaging surface and a dispenser and cutting blade for dental floss; all in one compact package. The dental floss may be stored out of sight either loose or on a spool. A top cover protects the loose end of the floss and provides a surface on which advertising may be imprinted. The top cover may contain a bezel with clear lens or may be made of a translucent or opaque material. The bottom surface of the combination toothpick, gum massager and dental floss holder also provides an additional area which advertising may be displayed.

3 Claims, 3 Drawing Figures

COMBINATION TOOTHPICK, GUM MASSAGER, AND DENTAL FLOSS HOLDER

BACKGROUND OF THE INVENTION

The present invention relates to dental appliances, and, more particularly, to a device for removing food particles and other foreign matter from between teeth and for massaging the gums.

While various types of toothpicks, floss and other cleaning devices have been provided for removing foreign matter from between the teeth, many have proven to be harmful and difficult to use.

Along with increased attention to periodontal disease as the major cause of loss of teeth in mature adults the practice of flossing has gained general approval as a prophylaxis. The present inventor, Carl J. Kucher, in U.S. Pat. No. 2,925,087 advanced the state of the art by providing a combined toothpick and gum massager which provides three separate though integrated utensils for removing food and foreign matter from between the teeth as well as an integral gum massager. However, this invention is somewhat lacking in that a user desiring the best prophylaxis would have to carry a separate spool of dental floss. This represents a considerable inconvenience.

SUMMARY OF THE INVENTION

It is, therefore, a primary object of the present invention to provide a combination toothpick, gum massager and dental floss holder, which has all the advantages of the combined toothpick and gum massager and also provides for easy storage and use of dental floss.

Another object is to provide a combination toothpick, gum massager and dental floss holder, which allows the storage of floss either on a spool or loosely.

Another object is to provide a combination toothpick, gum massager and dental floss holder, which has a floss cutting blade to facilitate cutting off a desired length of dental floss.

Another object is to provide a combination toothpick, gum massager and dental floss holder, which provides advertising space on its top cover or bottom side so that the invention may be used as a promotional piece. This top cover may be constructed as a top cover with bezel and lens, in which case, the advertising message may be printed or silk screened onto the clear lens or bottom side. Alternatively, the top cover or bottom side may be translucent, transparent, or opaque and the advertising message may be imprinted onto the top surface of the top cover or bottom side, or the advertising message may be printed on a suitable piece of paper and insert behind the lens if the lens is translucent, or transparent. If so desired the lens may be constructed so that it will magnify objects observed there through.

A yet further object is to provide a combination toothpick, gum massager and dental floss holder, in which the dental floss is concealed yet easily replaced. This is accomplished by recessing the dental floss into a dental floss container with hinged dental floss cover.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in specific construction illustrated and described within the scope of the appended claims.

BRIEF DESCRIPTION OF THE DRAWING FIGURES

The figures in the drawings are briefly described as follows.

DETAILED DESCRIPTION OF THE PREFERRED EMBODIMENTS

Figure 1:
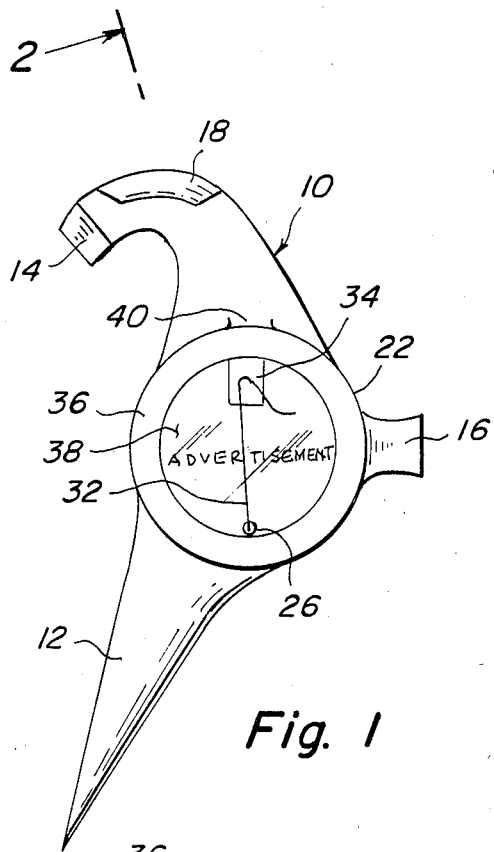
FIG. 1 is a top plan view of the invention.
Figure 3:
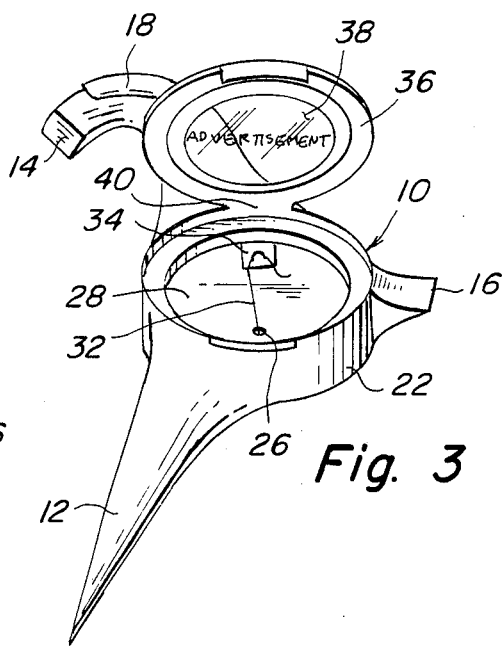
FIG. 3 is a perspective view thereof with the top cover open.

The basic structure of the invention 10 includes a toothpick section 12; two teeth cleaning surfaces 14 and 16; and a gum massager 18 radially located about main body portion 22.

Figure 2:
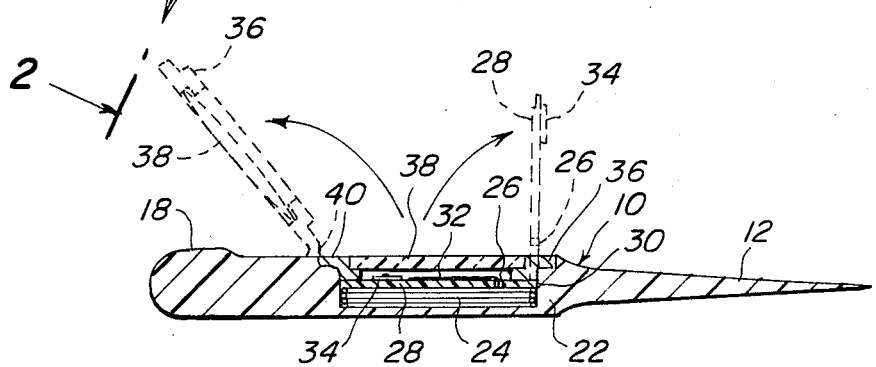
FIG. 2 is a cross sectional view taken on line 2—2 in FIG. 1.

A recess is provided in which dental floss 24 may be seen helically coiled. The loose end of dental floss 24 is threaded through aperture 26 in floss storage cover 28. Once the floss is threaded through the aperture, the floss storage cover 28, which is hinged by resilient hinge 30 may be snapped closed leaving just exposed end 32 showing. In FIG. 2 floss storage cover 28 is shown closed in solid lines and hinged open in phantom lines. The loose end of the floss 32 may be slid under floss cutting blade 34 and pulled sharply downward to cut the dental floss to the desired length.

A top cover with bezel 36 serves two functions. First, it protects the loose end of the dental floss 32 from becoming dislodged or pulled. Second, it provides a space for displaying an advertising message. This message may be displayed on clear lens 38, or, alternatively a translucent or opaque top cover may be used. This message may be either imprinted directly on the lens, or on a suitable paper insert (not illustrated), which is then affixed behind the lens so that the message may be seen there through a non opaque lens. In either case, the top cover 36 is hinged to main body portion 22 by a resilient hinge 40. In FIG. 2 top cover with bezel 36 and lens 38 are shown closed in solid lines and hinged open in phantom lines.

Similar advertising messages may be displayed on the bottom side of the device.

The lens 38 may be constructed so that objects observed there through are magnified as is well known in the art.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A combination toothpick, gum massager and dental floss holder comprising in combination:
   (a) a combined toothpick and gum massager comprising a main body portion, a short extension protruding radially outward from one edge of said main body portion, a hooklike extension protruding directly radially outwardly from the edge of said main body portion, circumferentially spaced from said short extension, a point extension protruding directly radially outwardly from the edge of said main body portion intermediate said short extension and said hook extension, said short extension including an outwardly facing thin edge for removing particles of food and foreign matter from between or around the incisor, canine, and premolar upper and lower teeth, said hook extension including an outwardly facing thin edge for removing food and foreign matter from between or around the upper and lower inside portions of all the teeth, and said point extension comprising a fine pick for removing food particles and foreign matter from between and around the upper and lower molars and wherein said hook extension further comprises an arcuate bulbous element for massaging the gums;

(b) means for useably storing a quantity of dental floss comprising a centrally located dental floss container recessed into said main body portion whereby dental floss may be directly placed into said dental floss container; a floss storage cover with an aperture through which dental floss may pass, wherein, said floss storage cover is hinged to said main body portion by a resilient integral hinge, a snap lock for said floss storage cover comprising a male portion and mating female portion, whereby said floss storage cover is locked and the spool and loosely gathered dental floss is protectively stored in the space provided for the spool and loosely gathered dental floss;

(c) means for cutting said dental floss to a desired length, comprising a floss cutting blade located on the top surface of said floss storage cover;

(d) means for protecting the free exposed end of said dental floss, comprising a top cover with bezel and lens which is hinged to said main body portion by a resilient hinge, and, a snap lock for said top cover with bezel and lens comprising a male portion and a mating female portion, whereby when said top cover with bezel and lens is locked said free end of said dental floss is protectively stored in the space between said floss storage cover and said top cover with bezel and lens, and (e) means associated with said top cover for providing advertising space whereby the advertisement can be viewed through the top cover.

2. A combination toothpick, gum massager and dental floss holder, as recited in claim 1, wherein said means for providing advertising space comprises a top cover whereby advertising copy and graphics depicted on said top cover may be viewed.

3. A combination toothpick, gum massager and dental floss holder, as recited in claim 1, wherein said means for providing advertising space on the bottom side whereby advertising copy and graphics depicted on said bottom side may be viewed.

* * * * *